(12) United States Patent
James

(10) Patent No.: US 7,373,820 B1
(45) Date of Patent: May 20, 2008

(54) ACCELEROMETER FOR DATA COLLECTION AND COMMUNICATION

(76) Inventor: Terry L. James, 840 Quail Rise, Fairview, Collin County, TX (US) 75069

(*) Notice: Subject to any disclaimer, the term of this patent is extended or adjusted under 35 U.S.C. 154(b) by 177 days.

(21) Appl. No.: 10/996,500

(22) Filed: Nov. 23, 2004

(51) Int. Cl.
*G01P 15/00* (2006.01)

(52) U.S. Cl. .................. 73/488; 340/573.1; 340/573.4; 73/530

(58) Field of Classification Search ............. 340/573.1, 340/573.4; 73/488
See application file for complete search history.

(56) References Cited

U.S. PATENT DOCUMENTS

| | | | |
|---|---|---|---|
| 5,593,431 A | 1/1997 | Sheldon | 607/19 |
| 5,649,968 A | 7/1997 | Alt et al. | 607/19 |
| 5,749,372 A | 5/1998 | Allen et al. | 128/782 |
| 5,807,283 A | 9/1998 | Ng | 600/595 |
| 5,885,231 A | 3/1999 | Cramer et al. | 600/595 |
| 5,899,963 A | 5/1999 | Hutchings | 702/145 |
| 5,919,149 A | 7/1999 | Allum | 600/595 |
| 5,925,001 A | 7/1999 | Hoyt et al. | 600/595 |
| 5,955,667 A | 9/1999 | Fyfe | 73/490 |
| 5,973,618 A | 10/1999 | Ellis | 340/990 |
| 5,976,083 A | 11/1999 | Richardson et al. | 600/300 |
| 6,032,530 A | 3/2000 | Hock | 73/379.01 |
| 6,052,654 A | 4/2000 | Gaudet et al. | 702/160 |
| 6,063,046 A | 5/2000 | Allum | 600/595 |
| 6,065,138 A | 5/2000 | Gould et al. | 714/47 |
| 6,095,991 A | 8/2000 | Krausman et al. | 600/595 |
| 6,122,340 A | 9/2000 | Darley et al. | 377/24.2 |
| 6,135,951 A | 10/2000 | Richardson et al. | 600/300 |
| 6,145,389 A | 11/2000 | Ebeling et al. | 73/865.4 |
| 6,168,569 B1 | 1/2001 | McEwen et al. | 600/557 |
| 6,273,856 B1 | 8/2001 | Sun et al. | 600/300 |
| 6,356,856 B1 | 3/2002 | Damen et al. | 702/160 |
| 6,377,179 B1* | 4/2002 | Fulton | 340/573.1 |
| 6,478,736 B1 | 11/2002 | Mault | 600/300 |
| 6,506,152 B1 | 1/2003 | Lackey et al. | 600/300 |
| 6,513,532 B2 | 2/2003 | Mault et al. | 128/921 |
| 6,571,200 B1 | 5/2003 | Mault | 702/182 |
| 6,578,291 B2 | 6/2003 | Hirsch et al. | 36/132 |
| 6,582,380 B2 | 6/2003 | Kazlausky et al. | 600/595 |
| 6,590,536 B1 | 7/2003 | Walton | 342/463 |
| 6,626,799 B2 | 9/2003 | Watterson et al. | 482/4 |
| 6,669,600 B2 | 12/2003 | Warner | 482/8 |
| 6,703,939 B2 | 3/2004 | Lehrman et al. | 340/669 |
| 6,714,133 B2 | 3/2004 | Hum et al. | 340/573.4 |
| 6,731,213 B1* | 5/2004 | Smith | 340/573.1 |
| 6,805,006 B2 | 10/2004 | Guzman | 73/490 |
| 6,807,869 B2 | 10/2004 | Farringdon et al. | 73/862.046 |
| 6,819,247 B2* | 11/2004 | Birnbach et al. | 340/573.1 |
| 6,825,777 B2* | 11/2004 | Vock et al. | 340/870.05 |

(Continued)

OTHER PUBLICATIONS

Diabetech, "News at Diabetech" http://www.diabetech.net (8 pages total), Aug. 27, 2004.

*Primary Examiner*—Hezron Williams
*Assistant Examiner*—Samir M. Shah
(74) *Attorney, Agent, or Firm*—Baker Botts L.L.P.

(57) ABSTRACT

A method for communicating data is provided that includes collecting data associated with an individual using an accelerometer. The accelerometer is operable to monitor activity associated with the individual. The method also includes communicating the data to a computing device, which can receive the data and perform any number of operations.

20 Claims, 4 Drawing Sheets

U.S. PATENT DOCUMENTS

| | | | |
|---|---|---|---|
| 6,878,121 B2 | 4/2005 | Krausman et al. | 600/587 |
| 6,918,858 B2 | 7/2005 | Watterson et al. | 482/54 |
| 6,997,852 B2 | 2/2006 | Watterson et al. | 482/1 |
| 6,997,882 B1 | 2/2006 | Parker et al. | 600/534 |
| 7,137,566 B2 * | 11/2006 | Silverbrook et al. | 235/494 |
| 7,156,289 B2 * | 1/2007 | Silverbrook et al. | 235/375 |
| 7,178,718 B2 * | 2/2007 | Silverbrook et al. | 235/375 |
| 7,181,448 B2 * | 2/2007 | Silverbrook et al. | 707/3 |
| 2001/0004234 A1 * | 6/2001 | Petelenz et al. | 340/539 |
| 2001/0048364 A1 * | 12/2001 | Kalthoff et al. | 340/573.1 |
| 2002/0109600 A1 * | 8/2002 | Mault et al. | 340/573.1 |
| 2003/0122677 A1 * | 7/2003 | Kail | 340/573.1 |
| 2003/0126593 A1 * | 7/2003 | Mault | 725/10 |
| 2003/0208110 A1 * | 11/2003 | Mault et al. | 600/300 |
| 2004/0130446 A1 * | 7/2004 | Chen et al. | 340/539.12 |
| 2004/0132461 A1 * | 7/2004 | Duncan | 455/456.1 |
| 2004/0133455 A1 | 7/2004 | McMahon | 705/3 |
| 2004/0249315 A1 | 12/2004 | Damen | 600/595 |
| 2005/0107723 A1 * | 5/2005 | Wehman et al. | 600/595 |
| 2005/0225868 A1 * | 10/2005 | Nelson et al. | 359/630 |

* cited by examiner

ACCELEROMETER FOR DATA COLLECTION AND COMMUNICATION

TECHNICAL FIELD OF THE INVENTION

This invention relates in general to communications and, more particularly, to an accelerometer for data collection and communication.

BACKGROUND OF THE INVENTION

Communication architectures have become increasingly important in today's society. In particular, the ability to quickly and accurately communicate collected data presents a significant obstacle for component manufacturers, system designers, and network operators. This obstacle is made even more difficult due to the plethora of diverse technologies that exist in the current market.

As new devices and electronic components become available to the consumer, new protocols need to be developed in order to appropriately interface with these emerging technologies. For example, certain devices may be ill equipped to interface with network components such that collected information cannot be suitable relayed over the Internet. In other scenarios, effective data transmission and data propagation present a complicated and an arduous task for the end user to complete. Without such interfacing capabilities, these new devices are stymied in their operations and inhibited in their performance, as they are unable to take full advantage of the benefits of complimentary components, which exist in the realm of communications.

SUMMARY OF THE INVENTION

From the foregoing, it may be appreciated by those skilled in the art that a need has arisen for an improved data collection and delivery process. In accordance with an embodiment of the present invention, a system and a method for collecting and transmitting data from an accelerometer are provided that substantially eliminate or greatly reduce disadvantages and problems associated with conventional data transmission strategies.

According to an embodiment of the present invention, a method for communicating data is provided that includes collecting data associated with an individual using an accelerometer. The accelerometer is operable to monitor activity associated with the individual. The method also includes communicating the data to a computing device, which can receive the data and perform any number of operations.

Certain embodiments of the present invention may provide a number of technical advantages. For example, according to one embodiment of the present invention, an architecture and process are provided that can be used to accurately collect data from a targeted patient. Moreover, such data collection may be performed stealthy, which requires no individual effort by the patient and which ensures the integrity of the information. This would allow precise measurements to be collected by an end user, administrator, physician, or nurse on behalf of the patient. High-quality data may be obtained through use of the architecture, as exact measurements may be executed in a systematic fashion. Such measurements may serve as a powerful tool in the context of identifying activity parameters for any given individual. The recorded measurements may also be used in the context of ascertaining performance data, such as is the case with performance athletes.

Certain embodiments of the present invention may enjoy some, all, or none of these advantages. Other technical advantages may be readily apparent to one skilled in the art from the following figures, description, and claims.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which.

DETAILED DESCRIPTION OF EXAMPLE EMBODIMENTS

Figure 1:
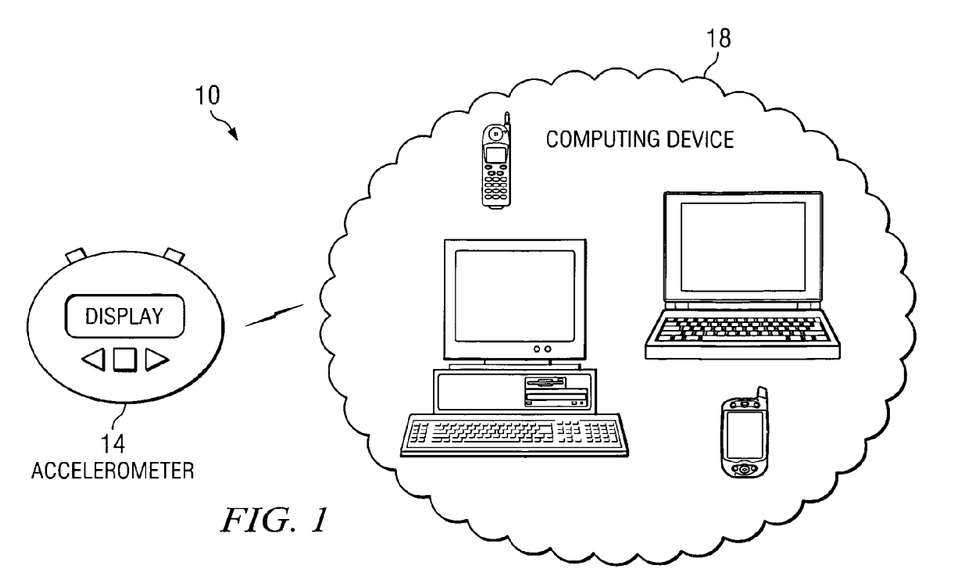
FIG. 1 is a simplified block diagram illustrating a communication system in accordance with one embodiment of the present invention.

FIG. 1 is a simplified block diagram of a communication system 10 for collecting, communicating, and transmitting data. Communication system 10 includes an accelerometer 14 and a computing device 18. These two elements may cooperate in order to exchange data collected from a given end user (not illustrated) that is using accelerometer 14. The end user may be an individual (e.g. a patient, an athletic person, an employee, etc.) that seeks to monitor his activity.

Accelerometer 14 is a device that is used to convert an acceleration from gravity or from motion into an electrical signal. The input for accelerometer 14 is generally gravity or motion. Accelerometer 14 can receive this input and provide an analog and/or a digital output that reflects this activity. Accelerometer 14 can measure acceleration in units of "g's". One "g" is defined as the earth's gravitational pull on an object or a person. For example, 1 g represents the acceleration exerted by the Earth's gravity on an object or person (for example, a cell phone on a desk experiences 1 g of acceleration). The acceleration range experienced by a person when walking is between 0.1-2.0 g. Accelerometer 14 may include a display, as well as any number of appropriate buttons that facilitate the operations thereof.

Computing device 18 is an element that includes hardware and/or software that is operable to receive activity data from accelerometer 14 (directly or indirectly). Computing device 18 may be accessed by any suitable authorized entity that seeks to review such information. Note that the term "computing device" encompasses a myriad of potential devices that may benefit from the operations of system 10. Computing device 28 may be a personal digital assistant (PDA), a cellular telephone, an Internet protocol (IP) telephone, a personal computer, a laptop computer, or any other suitable device or element that is operable to receive end user data collected by accelerometer 14. FIG. 1 illustrates only one set of example devices that may be used within communication system 10. The present invention is replete with numerous alternatives that could be used to receive the collected information.

It should be noted that the internal structure of accelerometer 14 and computing device 18 are malleable and can be readily changed, modified, rearranged, or reconfigured in order to achieve their intended operations. As identified supra, software and/or hardware may reside in computing device 18 and/or in accelerometer 14 in order to achieve the teachings of the communication exchange feature of the present invention. The software and/or hardware may also be used to offer other features such as global positioning system (GPS) sensing, geo-fencing, and triangulation protocols that may be used to exchange data (e.g. activity data collected by accelerometer 14) and/or to identify the location of the end user. All such capabilities of these elements, as well as the others outlined herein, may be provided within accelerometer 14 and/or computing device 18 to achieve such operations. However, due to their flexibility, these two elements may alternatively be equipped with (or include) any suitable component, device, application specific integrated circuit (ASIC), processor, microprocessor, algorithm, read-only memory (ROM) element, random access memory (RAM) element, erasable programmable ROM (EPROM), electrically erasable programmable ROM (EEPROM), field-programmable gate array (FPGA), or any other suitable element or object that is operable to facilitate the operations thereof. Considerable flexibility is provided by the structure of computing device 18 in the context of communication system 10.

For purposes of teaching and discussion, it is useful to provide some overview as to the way in which the following invention operates. The following foundational information may be viewed as a basis from which the present invention may be properly explained. Such information is offered earnestly for purposes of explanation only and, accordingly, should not be construed in any way to limit the broad scope of the present invention and its potential applications.

Physical inactivity is a major risk factor for a multitude of illnesses. Precise quantification of physical activity is critical in any environment, whether it be in the realm of heightened physical fitness or in situations where some individual is in poor health. Physical activity is especially important in measuring the outcomes in frail, sedentary populations, and in the elderly, because small improvements in physical functioning such as walking and balance may translate into significantly improved higher-order function and life quality. Nonetheless, although daily monitoring of physical activity is of great interest to investigators and clinicians alike, methods to precisely measure this vital dimension of function have only been recently available.

Methods in current use for measuring daily activity include direct observation, self-report questionnaires and diaries, radioisotope techniques (doubly-labeled water measurement of energy expenditure), and heart-rate monitoring. These methods suffer from several problems. Direct observation is both time-consuming and intrusive, and self-report questionnaires and diaries that rely on memory are imprecise (especially in the elderly) and are time-intensive for subjects. Radioisotope methodology is both costly and technologically complex. Heart-rate monitoring is both expensive and imprecise in patients whose heart rates may vary due to medication use and other causes unrelated to physical activity. In addition, neither radioisotope and heart-rate monitoring technologies are capable of providing information on specific patterning of activity.

Accelerometer movement sensors are a practical alternative to other methods, providing a high degree of precision across a wide range of activity levels at a relatively low cost. Single-axis accelerometers measure movement in one plane and have been widely used to study physical activity and energy consumption in healthy young people and the elderly. In addition to having only one plane of measurement, a major disadvantage of some accelerometers is inadequate data storage and retrieval technology, which requires study subjects to read and record output from the device when measurement is carried out over days.

More recently, a new generation of multi-axis accelerometers have been developed that have improved sensitivity and are more suitable for research purposes. (Note that accelerometer 14 may be a single plane, dual-plane, tri-plane, or multi-plane device.) These devices have been compared to doubly labeled water to study energy expenditure in normal, active people, and to study activity in relatively sedentary clinical populations, including nursing home residents, outpatients with multiple sclerosis (MS), and obese children.

Accelerometer measurement of walking would assist greatly in clarifying the role of walking behavior as a marker and perhaps determinant of physical functioning in the elderly and persons with chronic illness. Walking is the activity targeted for improvement in most pulmonary rehabilitation programs and other health-maintenance regimens aimed at improving physical functioning, prolonging life, and preventing illness associated with sedentary living. In other scenarios, accelerometer measurements of running sessions or workouts provide an invaluable training tool for the serious athlete. Accelerometer 14 can accurately gauge activity associated with vigorous training regimens. In addition, the collected data may serve as a terrific training log for any athlete, as his progress and daily energy expenditures may readily be determined.

When looking at energy utilization, there are generally four types of approaches for measuring energy expended by an individual, they are: 1) oxygen consumption; 2) heart-rate monitoring; 3) pedometers; and 4) accelerometers. Pedometers are highly inaccurate, heart-rate monitoring measurements are often skewed (e.g. due to conditioning, deconditioning, drugs, etc.), and direct oxygen consumption measurements are time-consuming, cumbersome, and expensive. Hence, accelerometers provide a viable alternative to these flawed devices.

Figure 2:
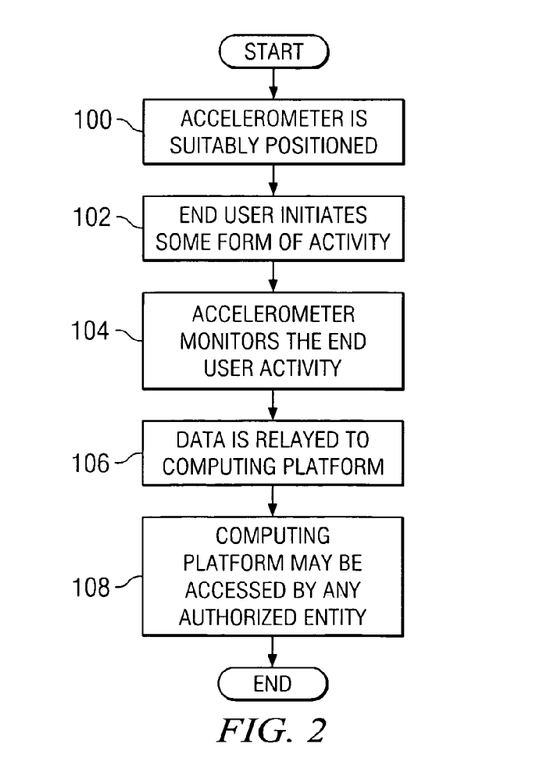
FIG. 2 is a simplified flowchart illustrating a number of example steps associated with a method of the communication system of FIG. 1.

FIG. 2 is a simplified flowchart illustrating a number of example steps associated with a method to be performed within communication system 10. The flowchart begins at step 100, where accelerometer 14 is suitably positioned on an end user, a patient, an employee, or any other targeted individual. At step 102, the end user initiates some activity such as walking or running. Alternatively, the end user may simply be moving about such that some form of exercise is being performed and the corresponding data recorded.

As the end user participates in some form of activity, accelerometer 14 monitors the end user activity and records all data readings that are recognized. This is illustrated by step 104. Accelerometer 14 may be turned to an ON position by the end user in order to track such movement, or the device itself may be autonomous in responding to some form of movement. At step 106, the collected data may be relayed to any suitable computing platform (such as computing device 18). This may be achieved in a wireless fashion (as detailed below) or via a modem, a universal serial bus (USB) connection, or any other suitable connection, link, or port.

At step 108, the collected data may be accessed by any suitable entity authorized to do so. For example, the end user himself may review the collected data via his home personal computer. In other scenarios, an employer may seek to review this collected data. In still other scenarios, a provider of healthcare may wish to ascertain this information. The collected data may be presented to these entities in any suitable format: having any appropriate organization, which may be based on user preferences.

Note that the benefit of exercise has been well-documented. However, this descriptive information has not been quantified. For example, a study could suggest that the occurrence of breast cancer could be reduced significantly if exercise was increased in the target population. But the bigger question would be: what level of activity would solicit this positive response? Hence, accelerometer readings should be translated into some metric that provides a tool for ascertaining activity levels. Activity values, which could represent energy expended or energy intensity, could then be correlated to some level of fitness. This would allow activity to be quantified for individuals and groups. Hence, the exercise component and the health benefits of various states can be accurately quantified. This would offer a powerful tool in evaluating the correlation between activity and health.

In addition, an overall activity level of an individual or a group could be readily determined. This would allow for a correlation of health care costs (i.e. associated medical costs) and activity levels for various groups. Also, productivity levels could be correlated to activity levels identified through accelerometer 14. The measurements of accelerometer 14 could be used to provide a verifiable metric for comparing any number of various characteristics amongst individuals or groups.

Figure 3:
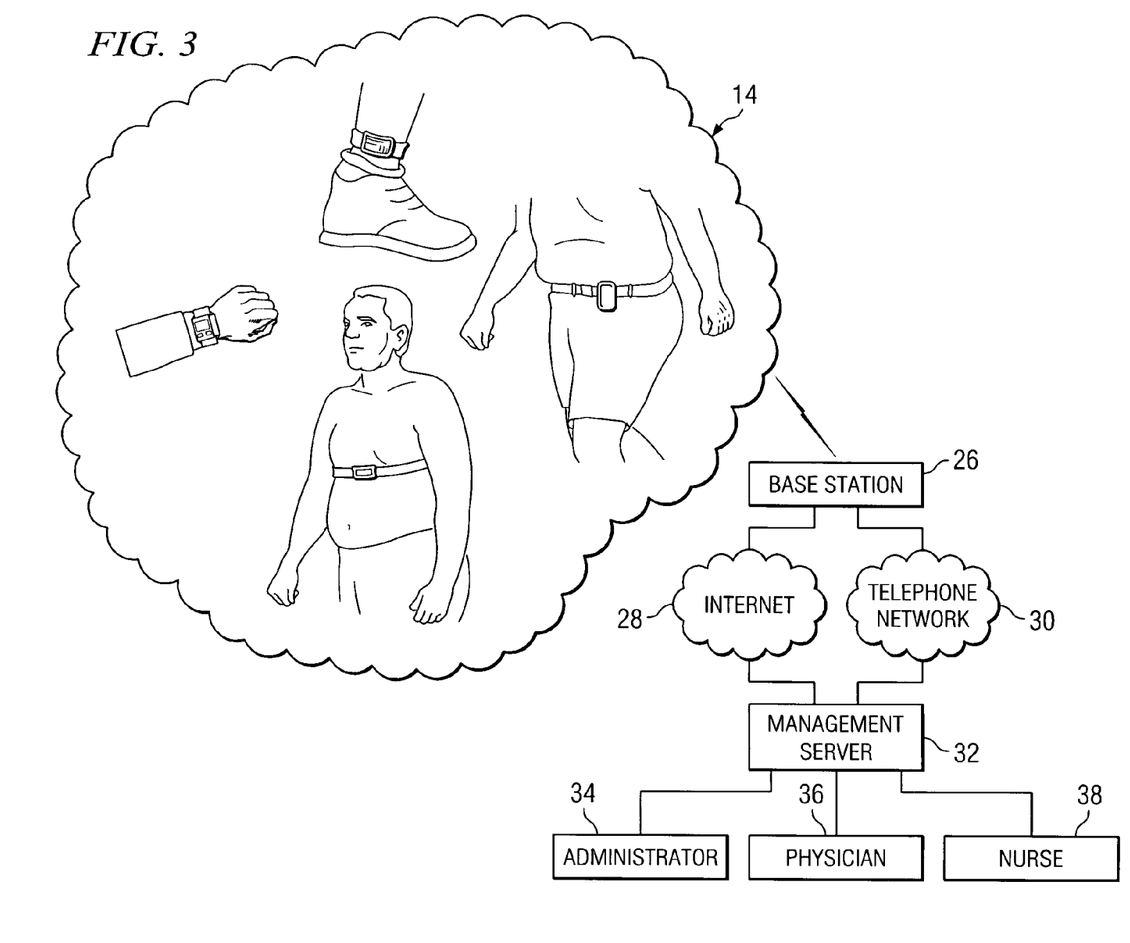
FIG. 3 is a simplified schematic diagram of an example communication architecture that may be used in the communication system.

FIG. 3 is a simplified schematic diagram of an example wireless communication architecture that may be used in communication system 10. Other embodiments may use other non-wireless connections, as described more fully herein. The arrangement features the use of a number of accelerometers 14 that can be used in any number of configurations (e.g. strapped to an end user's chest, ankle, wrist, belt, etc.). FIG. 3 may also include a base station 26, which represents a type of computing device 18. The illustrated architecture may also include an Internet 28, a telephone network 30, a management server 32, an administrator 34, a physician 36, and a nurse 38.

These elements may cooperate in order to stealthy collect patient data in this example. Accelerometers 14 can be issued to selected individuals (e.g. students or employees) or patients. Accelerometers 14 may be worn continuously by the selected individuals or only worn during certain times, such as during exercise activities being completed by the individual.

In one embodiment, a blue tooth chip may be provided in each accelerometer 14 such that data may be collected from the patient in a manner that requires no effort from the individual. Blue tooth, also referred to as IEEE 802.15, generally uses the radio waves located in the frequency band of 2.4 GHz (2400 to 2483.5 MHz). In this band, blue tooth can transmit voice and data at flows lower than one megabit per second. The blue tooth devices generally can function in two modes: 1) circuit switched (the most common mode for voice communications and wireless digital networks); and 2) packet switched (the mode for Internet data, as well as for higher bandwidth mobile communication systems (e.g. General Packet Radio Service (GPRS)).

A given accelerometer 14 can use either one or both of these modes or use some other appropriate blue tooth application. In packet switched mode, the connection is asynchronous with a rising flow of 57.6 Kbps to 721 Kbps. In the second mode, the connection is synchronous with a flow of approximately 64 Kbps. In operation, blue tooth behaves as a wireless personal area networking (PAN) technology that allows devices to connect (e.g. with base station 26) in a range of approximately 33 feet (10 meters) up to 100 meters with approximately 0 to 20 dBm output power. Thus, accelerometers 14 within the proximity of base station 26 may readily transmit data in a quick and an accurate manner.

The blue tooth technology allows for a systematic and a covert retrieval of patient data. The data itself is highly accurate, as the integrity of the data is maintained as it traverses a pathway that leads to management server 32, which can aggregate any number of data sets collected by accelerometer 14. The data sets could represent a group of individuals who are using one or more accelerometers 14. The key is to capture the data with little effort from the patient. One concern is to alleviate the patient from the obligation of logging information, but the more important concern is to provide the ability to collect high quality data. As described above, self-reported data is problematic, as it is often incorrect and skewed.

In alternative scenarios, other wireless forms of communication could also be accommodated by the present invention. For example, infrared systems, laser technologies, bar-coding scenarios, and any other suitable technologies could be implemented in cooperation with the teachings of the present invention. In still other embodiments, a cable could be used in combination with accelerometer 14. For example, a simple USB port from a computer could be used to deliver data from accelerometer 14 to a home computer. The home computer could then relay the data, via Internet 28 or telephone network 30, to management server 32. Hence, these scenarios would allow for wireless or wired embodiments of the present invention or direct base station applications.

For example, in other embodiments a cable could be used to plug directly into base station 26. In still other embodiments, a series of docking stations or cradles could be provided in conjunction with accelerometers 14. The docking stations could receive accelerometer 14 and automatically download the collected data. The data exchange could be done quickly such that the patient or individual is minimally burdened with such a task.

Each accelerometer 14 may also include the ability to uniquely identify the user of the device. Each accelerometer 14 could also be capable of storing information and providing feedback to the user. For example, the feedback could include (e.g. text, graphic, video, sound, etc.) messages such as: "goal accomplished," "please slow down as you are exceeding your recommended activity range," or any other suitable message, alert, or signal that can be understood by the user. Thus, each accelerometer 14 may include an ability to store the patient data, as well as some type of technology that can transmit the recorded patient data to base station 26. Accordingly, accelerometers 14 may include any suitable hardware, software, memory units, components, elements, or objects that may be utilized or implemented to achieve the operations and functions described herein Base station 26 is an element that is equipped with electronics that are capable of interfacing with accelerometers 14. Base station 26 could readily accommodate a wireless transmission from accelerometer 14 to base station 26. In one embodiment (particular to a blue tooth application), base station 26 could include a blue tooth chip, a central processing unit (CPU), and a modem. In alternative embodiments, base station 26 could include any other suitable technology that facilitates the reception of patient data from accelerometers 14. Alternatively, base station 26 may also include any other appropriate hardware, software, algorithms, processors, EEPROMs, EPROMs, or any other suitable elements that facilitate their operations. Such alternative configurations may be based on particular communication needs. Moreover, in other embodiments, all of the elements of FIG. 3 may be provided in any suitable ASICs, application intervention interfaces (APIs), elements, or objects (or any suitable combination of these elements) operable to facilitate the operations thereof.

The modem included in base station 26 could connect (via a telephone line (through telephone network 30) or Internet 28) to management server 32, which could receive the data. The provided technology (e.g. blue tooth, infrared, barcoding, etc.) allows base station 26 to be transformed from a local area network (LAN) to a wide area network (WAN). Thus, base station 26 can collect data locally from accelerometer 14 and then relay that information in a WAN-like manner via Internet 28 and telephone network 30. Management server 32 could collect all the patient data and organize it in any appropriate fashion. Such data propagation methods could be performed with minimal expense for their associated transmissions.

Internet 28 and telephone network 30 are intermediary links that are used to deliver data collected from accelerometers 14. These elements may be replaced by any metropolitan area network (MAN), wireless local area network (WLAN), or any other appropriate architecture or system that facilitates communications in a network or a telephone environment. Internet 28 may include any suitable connection (e.g. dial-up, digital subscriber line (DSL), cable, etc.) to facilitate the delivery of data.

Once the data is collected by management server 32, any suitable application could then be executed using the collected information. For example, the data could be collected by management server 32 and then relayed to physician 36 or nurse 38, who could then review the results. Physician 36 or nurse 38 could then send a feedback message back through the system (e.g. via base station 26 to accelerometer 14) such that the patient could view the message. In other scenarios, physician 36 or nurse 38 could simply transfer the information to a patient chart or log for future review. In still other scenarios, the collected data may be delivered to a trainer or coach that reviews the activity information and then offers suitable feedback to the end user.

Other applications could include a simple patient log that is maintained by management server 32 automatically. Management server 32 may store personal records for the participating individuals, comparisons between (for example) departments, age groups, etc., and offer a place for administrator 34 to evaluate and to review the collected data. In addition, administrator 34 (who may need to use a log-in prompt and corresponding password) can oversee the progress of each individual and create his own graphs, charts, records, etc. In contrast to other health paradigms that may monitor critical levels of a patient weekly or monthly (e.g. through in-office doctor visits), such applications could generate a record and a printout that reflects patient levels being recorded several times per-day. Improvements or deteriorations in the patient could then readily be identified. Because of their extensive operations, management server 32 may include any suitable hardware, software, devices, components, algorithms, EEPROMs, EPROMs, elements, or objects that may be utilized or implemented to achieve the operations and functions described herein. Alternatively, other configurations of management server 32 may include any other suitable elements that are based on particular communication needs. In addition, the term "management server" may encompass any suitable network or electronic devices that are operable to perform the functions described herein. Such devices may include databases, host computers, and processors, for example.

It should be noted that the internal structure of the system of FIG. 3 is malleable and can be readily changed, modified, rearranged, or reconfigured in order to achieve its intended operations or additional operations. Additionally, any of the items within FIG. 3 may be combined, where appropriate, or replaced with other functional elements that are operable to achieve any of the operations described herein.

Figure 4:
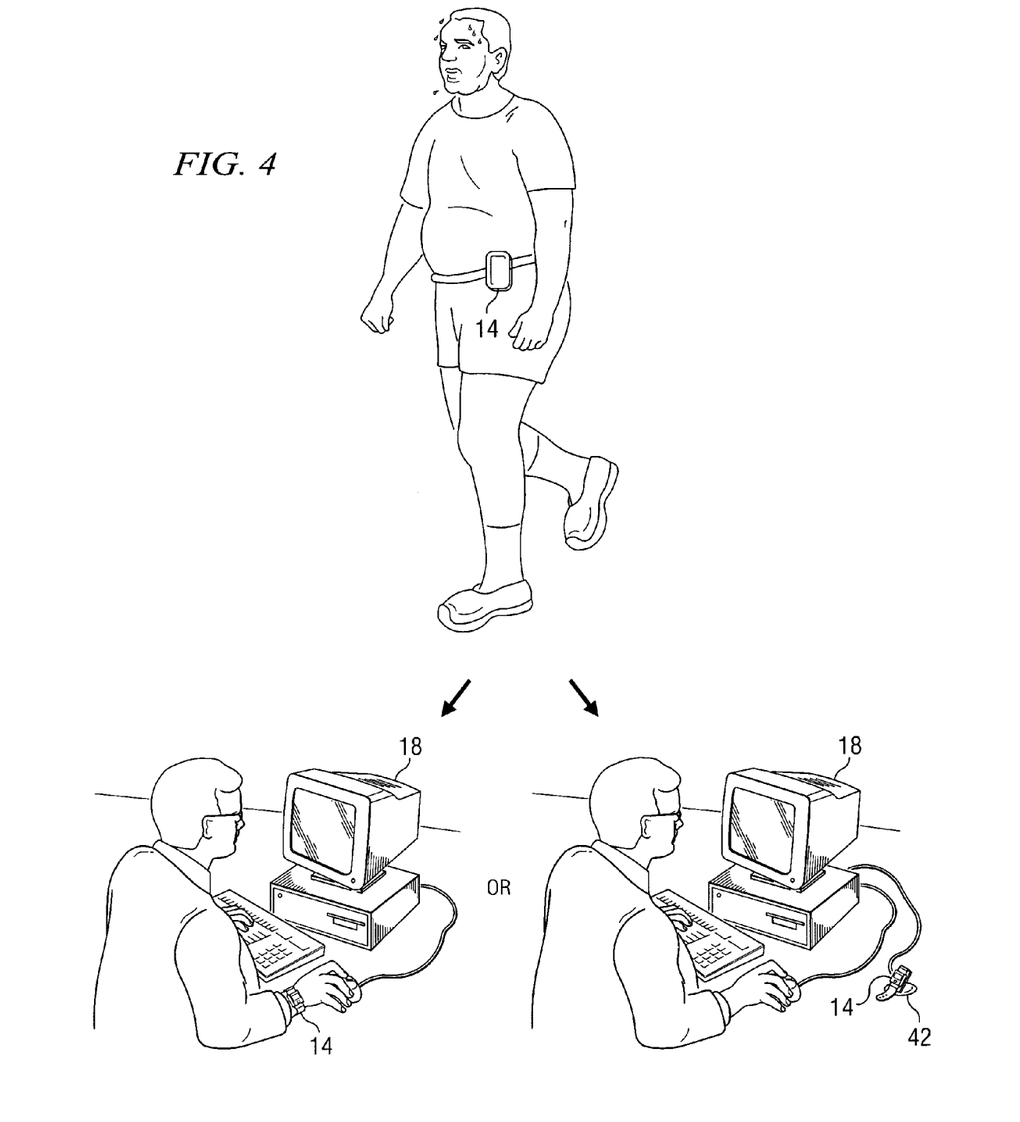
FIG. 4 is a simplified schematic diagram of an example operation of the communication system.
Figure 5:
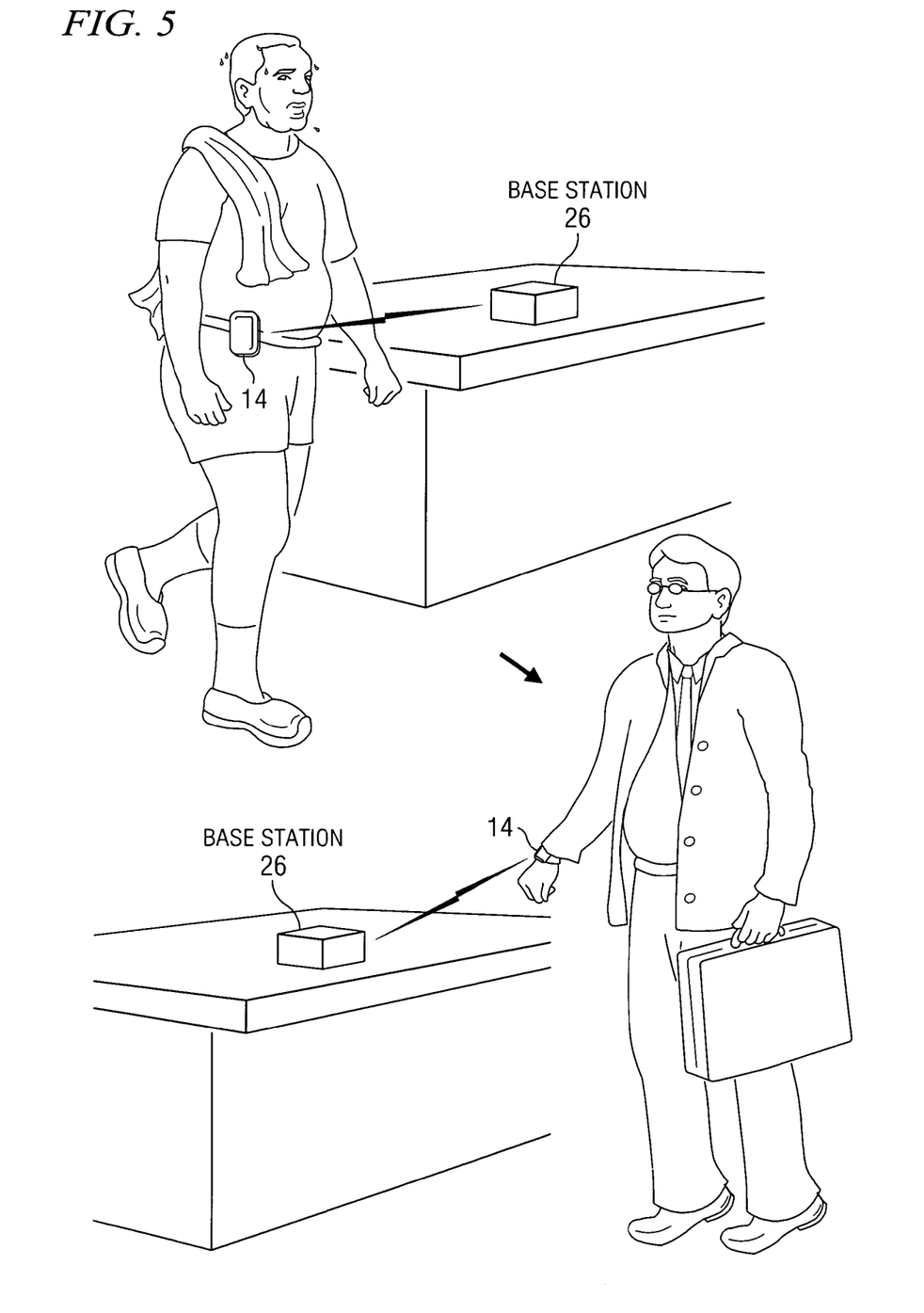
FIG. 5 is a simplified schematic diagram of another example operation of the communication system.

FIGS. 4 and 5 are simplified schematic diagrams of example operations of communication system 10. Both FIG. 4 and FIG. 5 depict example stages of the present invention, whereby these schematic show two example scenarios that involve one individual, who is exercising and another that is simply working at his job. In the example embodiment of FIG. 4, the individual is participating in an exercise program. Accelerometer 14 tracks the end user's movement during his exercise. Once the end user completes his exercise, he then returns to his home and downloads the collected data to computing device 18. In the alternative scenario that is illustrated, a docketing station 42 is provided to receive accelerometer 14. Once positioned in docketing station 42, accelerometer 14 may transmit the stored information automatically to any suitable next destination.

Turning to FIG. 5, the end user is again participating in an exercise regimen (perhaps during his lunch break at a local gym). In this case however, the end user simply walks past a given base station 26 (which reflects a type of computing device 18) such that his data is relayed directly to base station 26. In this scenario, base station 26 is strategically positioned such that the patient is not even aware of the data transmission. The data that is collected is relayed to base station 26: unbeknownst to the end user. This scenario illustrates an example work environment in which data can be routinely collected while the individual is completing his daily tasks. Note that the two scenarios of FIGS. 4 and 5 offer just a couple of the possible arrangements for an end user to benefit from the teachings of the present invention. Alternatively, base station 26 could be positioned in any suitable location such that the collected data may propagate from accelerometer 14 to base station 26.

The aggregation of any incoming data from the operations of FIGS. 4 and 5 may be executed by management server 32. Management server 32 may receive such data via Internet 28 or telephone network 30, as illustrated in FIG. 3. Management server 32 may be positioned in any suitable location such that it can properly receive the incoming patient data. Management server 32 may be coupled to Internet 28 and/or telephone network 30 or coupled to any other link or device such that it can receive the raw patient data.

As outlined above, the collected data reflects a general compilation of end user data that may be organized in any format. The decision as to the format, organization, and display of the data may be executed by administrator 34, physician 36, nurse 38, or the end user himself. The collected data may be stored within management server 32 or stored in any other appropriate location. In addition, any number of programs may be run on the collected data in order to produce desired outputs and resultants. For example, the collected data (e.g. displayed and stored in computing device 18 or management server 32) can be used as a basis for comparisons, graphs, charts, spreadsheets, or any other graphical illustrations or profiles based on particular needs. In other embodiments, the collected data may automatically trigger any suitable message to be sent to the end user. For example, certain messages may be related to encouragement or alerts about over-exertion. Hence, other messages could relate to warnings for the patient to reduce or increase his levels of activity, walking, etc. Considerable flexibility is offered by such messaging scenarios.

It is important to note that the stages and steps in FIGS. 2 through 5 illustrate only some of the possible scenarios that may be executed by, or within, the present system. Some of these stages and/or steps may be deleted or removed where appropriate, or these stages and/or steps may be modified or changed considerably without departing from the scope of the present invention. In addition, a number of these operations have been described as being executed concurrently with, or in parallel to, one or more additional operations. However, the timing of these operations may be altered. The preceding example flows have been offered for purposes of teaching and discussion. Substantial flexibility is provided by the tendered architecture in that any suitable arrangements, chronologies, configurations, and timing mechanisms may be provided without departing from the broad scope of the present invention.

Note that the example embodiments described above can be replaced with a number of potential alternatives where appropriate. The processes and configurations discussed herein only offer some of the numerous potential applications of system 10. The elements and operations listed in FIGS. 1-5 may be achieved with use of system 10 in any number of contexts and applications. Accordingly, communications capabilities, data processing features and elements, suitable infrastructure, adequate personnel and management, and any other appropriate software, hardware, or data storage objects may be included within system 10 to effectuate the tasks and operations of the elements and activities associated with managing healthcare costs.

Numerous other changes, substitutions, variations, alterations, and modifications may be ascertained to one skilled in the art and it is intended that the present invention encompass all such changes, substitutions, variations, alterations, and modifications as falling within the spirit and scope of the appended claims. In order to assist the United States Patent and Trademark Office (USPTO) and additionally any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of filing hereof unless the words "means for" are specifically used in the particular claims; and (b) does not intend by any statement in the specification to limit his invention in any way that is not otherwise reflected in the appended claims.

What is claimed is:

1. A method for communicating data, comprising:
 collecting data associated with an individual using an accelerometer, wherein the accelerometer is operable to monitor activity associated with the individual, and wherein the data is only accessible by persons authorized to do so, whereby the accelerometer provides feedback to the individual based on a combination of the collected data and additional data that is unique to the individual, the additional data being associated with a profile of the individual, and whereby activity calculations made by the accelerometer are based on a conversion of gravity or of motion to an electrical signal; and
 communicating the data to a computing device, wherein the accelerometer uniquely identifies the individual, and wherein a decision to display the data is executed by an administrator of the device.

2. The method of claim 1, further comprising:
 accessing the data from the computing device.

3. The method of claim 1, further comprising:
 displaying at least a portion of the data on the accelerometer to the individual.

4. The method of claim 1, further comprising:
 maintaining the data such that it can be transmitted over a communication link.

5. The method of claim 4, wherein the communication link is a selected one of a group of communication links, the group consisting of:
 a) a universal serial bus cable;
 b) a modem; and
 c) a wireless connection.

6. The method of claim 1, wherein the data from the accelerometer is communicated to the computing device using IEEE 802.15 protocol.

7. The method of claim 1, further comprising:
 storing the data such that it may be reviewed, wherein the stored data may be processed using one or more software applications.

8. The method of claim 1, further comprising:
 communicating a selected one of location information and activity information provided by the accelerometer using a selected one of a group of protocols, the group consisting of:
 a) a global positioning system (GPS) protocol;
 b) a geo-fencing protocol; and
 c) a triangulation protocol.

9. An apparatus to be used in collecting data, comprising:
 an accelerometer operable to monitor activity associated with an individual, the accelerometer being operable to collect and to store data associated with the activity, wherein the accelerometer is further operable to communicate the data to a computing device, and wherein the data is only accessible by persons authorized to do so, whereby the accelerometer provides feedback to the individual based on a combination of the collected data and additional data that is unique to the individual, the additional data being associated with a profile of the individual, and whereby activity calculations made by the accelerometer are based on a conversion of gravity or of motion to an electrical signal; and
 wherein the accelerometer uniquely identifies the individual, and wherein a decision to display the data is executed by an administrator of the device.

10. The apparatus of claim 9, wherein the computing device is a base station operable to receive the data from the accelerometer, the base station being further operable to relay the data to a next destination via a selected one of a telephone network and an Internet network.

11. The apparatus of claim 9, wherein the accelerometer includes a display that is operable to provide one or more activity measurements obtained by the accelerometer.

12. The apparatus of claim 9, wherein the accelerometer is operable to maintain the data such that it can be transmitted over a communication link.

13. The apparatus of claim 12, wherein the communication link is a selected one of a group of communication links, the group consisting of:
 a) a universal serial bus cable;
 b) a modem; and
 c) a wireless connection.

14. The apparatus of claim 9, wherein the computing device is further operable to store the data such that it may be accessed and reviewed.

15. The apparatus of claim 9, wherein the accelerometer includes wireless technology that is operable to transmit the data to a next destination in a wireless fashion, the wireless technology being included in a group of technologies, the group consisting of:
   a) IEEE 802.15 technology; and
   b) infrared technology.

16. The apparatus of claim 9, wherein the accelerometer is further operable to communicate a selected one of location information and activity information included within the accelerometer using a selected one of a group of protocols, the group consisting of:
   a) a global positioning system (GPS) protocol;
   b) a geo-fencing protocol; and
   c) a triangulation protocol.

17. The apparatus of claim 9, further comprising:
   a management server operable to receive the data from the accelerometer and to aggregate one or more sets of data collected by the accelerometer.

18. The apparatus of claim 17, wherein the management server is operable to be accessed by a selected one of a physician, a nurse, and an administrator who is authorized to have access to the data.

19. The apparatus of claim 9, wherein the accelerometer is distributed to a group of persons, the group being a selected one of a plurality of employees in a work environment, a plurality of patients in a healthcare environment, and a plurality of students in a school environment.

20. The apparatus of claim 9, wherein the data is processed using one or more software applications at the computing device, and wherein the data may be displayed on the computing device using a selected one or more of a graph, a chart, a spreadsheet, and a graphic illustration.

* * * * *